US00RE38202E

(19) United States
(12) Reissued Patent
Mertens et al.

(10) Patent Number: US RE38,202 E
(45) Date of Reissued Patent: Jul. 22, 2003

(54) ANTIBODIES SPECIFIC FOR A HAEMOSTATIC PROTEIN, THEIR USE FOR ISOLATING PROTEIN, HAEMOSTATIC COMPOSITIONS DEVOID OF PROTEOLYTIC CLEAVAGE PRODUCTS OF THE PROTEIN

(75) Inventors: Koenraad Mertens, Leiden (NL); Jan Aart van Mourik, Badhoevedorp (NL)

(73) Assignee: Stichting Sanquin Bloedvoorziening, Amsterdam (NL)

(21) Appl. No.: 09/618,592

(22) Filed: Jul. 17, 2000

Related U.S. Patent Documents

Reissue of:
(64) Patent No.: 5,932,706
Issued: Aug. 3, 1999
Appl. No.: 08/797,842
Filed: Feb. 10, 1997

U.S. Applications:
(63) Continuation of application No. 08/381,891, filed as application No. PCT/NL93/00174 on Aug. 26, 1993, now abandoned.

(30) Foreign Application Priority Data

Aug. 27, 1992 (EP) ..... 92202615

(51) Int. Cl.[7] ..... A61K 39/395
(52) U.S. Cl. ..... 530/413; 530/388.25; 530/389.3
(58) Field of Search ..... 530/388.25, 389.3, 530/412, 413; 435/70.21; 436/824

(56) References Cited

U.S. PATENT DOCUMENTS 5,055,557 A * 10/1991 Zimmerman ..... 530/381
5,252,712 A * 10/1993 Furie et al. ..... 530/389.3
5,336,610 A * 8/1994 Esmon et al. ..... 435/212

FOREIGN PATENT DOCUMENTS

WO 90/06501 * 5/1991

OTHER PUBLICATIONS

Pelzer et al. Thrombosis and Haemostasis, 65(2):153–159, 1991.*

New Riverside Dictionary, Webster's II, fifth ed., p. 622, Riverside Publishing Company, 1994.*

Theodorsson et al. Blood:61(5):973–981, 1983.*

Lerner, R.A. Nature 299:592–596, 1982.*

Verlander et al. Biotechnology Progress:5(3):119–125, 1989.*

Furie et al., Cell, 53:505–518, May 1988.*

Huang et al., Blood, 73(3):718–721, Feb. 1989.*

Taylor et al., British Journal of Haematology, 75(2):217–221, Jun. 1990.*

Smith et al., Thrombosis Research 33:211–224, 1984.*

* cited by examiner

*Primary Examiner*—Brenda Brumback
(74) *Attorney, Agent, or Firm*—Hoffmann & Baron, LLP

(57) ABSTRACT

A method for the generation of Ca++ independent antibodies against blood coagulation factors is described wherein an antibody selection strategy based upon small peptides comprising target sequences for limited proteolysis is employed. These antibodies which distinguish between intact and cleaved species of haemostatic protein provide novel tools for the isolation of intact haemostatic proteins.

18 Claims, No Drawings

ANTIBODIES SPECIFIC FOR A HAEMOSTATIC PROTEIN, THEIR USE FOR ISOLATING PROTEIN, HAEMOSTATIC COMPOSITIONS DEVOID OF PROTEOLYTIC CLEAVAGE PRODUCTS OF THE PROTEIN

Matter enclosed in heavy brackets [ ] appears in the original patent but forms no part of this reissue specification; matter printed in italics indicates the additions made by reissue.

This application *and copending application No. 10/228,882 are both reissues of patent application Ser. No. 08/797,842, U.S. Pat. No. 5,932,706, which* is a continuation of our co-pending patent application filed on Feb. 8, 1995, assigned Ser. No. 08/381,891, now abandoned and entitled "Antibodies Specific for a Haemostatic Protein. Their Use for Isolating Intact Protein. Haemostatic Compositions Devoid of Proteolytic Cleavage Products of the Protein which is 371 of PCT of PCT/NL93/00174 filed Aug. 26, 1993.

FIELD OF THE INVENTION

This invention relates to the preparation of therapeutic compositions consisting of purified blood coagulation factors for the treatment of haemostatic disorders. Said compositions are obtained by affinity chromatography employing antibodies, more in particular monoclonal antibodies, that distinguish between intact and cleaved molecular species. Methods are disclosed to obtain such antibodies, which allow the isolation of vitamin K-dependent blood coagulation proteins, including Factor IX, Factor VII, Protein C or Protein S, as intact polypeptides, devoid of cleavage products representing activated or degraded species.

BACKGROUND OF THE INVENTION

Inherited or acquired deficiencies of proteins of the blood coagulation system provide a major cause for the occurrence of haemostatic disorders. Even the lack or shortage of one single component of this system may be sufficient to disturb the delicate balance between procoagulant and anticoagulant pathways in a manner resulting in major clinical signs of bleeding or thrombosis. One of the most common bleeding disorders is Haemophilia A, which is due to deficiency or dysfunction of the coagulation Factor VIII. Less frequently occurring, but equally severe bleeding disorders include deficiencies of the haemostatic proteins Factor IX (Haemophilia B), Factor VII, or Factor X. On the other hand, thrombosis may occur as the result of even partial (heterozygous or acquired) deficiency of Protein C or Protein S, which are major components of a system that acts as an antagonist of the coagulation pathway (for reviews on haemostatic disorders see A. L. Bloom and D. P. Thomas (Eds.), Haemostasis and Thrombosis, 2nd edition, Churchill-Livingstone, Edinburgh, 1987, pp 393–436 and 452–464). Replacement therapy is considered as a powerful and effective means to restore the haemostatic balance in vivo. For instance, concentrates containing Factor IX have proven highly valuable blood products which are life-saving when used to control bleeding in patients suffering from Factor IX deficiency.

Commercially available Factor IX concentrates (so-called prothrombin complex concentrates) usually are prepared with ion exchange resins to separate Factor IX from the other plasma proteins. This technique however, yields Factor IX preparations that also contain a number of other, closely related haemostatic proteins. These include Factor VII, Factor X, Factor II, Protein C and Protein S, which all belong to the class of the vitamin K-dependent proteins. The term "vitamin K-dependent" is referring to the fact that these proteins contain glutamic acid residues that are carboxylated during biosynthesis in a vitamin K-dependent process. Carboxylation provides these proteins with unique $Ca^{2+}$-binding sites that are obligatory for the biological activity of these proteins within the $Ca^{2+}$-dependent haemostatic process. Due to these and other structural similarities (see B. Furie and B. C. Furie, Cell vol 53, 1988, pp 505–518), the vitamin K-dependent proteins are readily co-purified. Thus, most Factor IX concentrates are also containing other haemostatic proteins such as Factor VII, Protein C and Protein S, and consequently the same concentrates have been used for the treatment of deficiencies of those proteins as well. However, treatment of bleeding disorders with compositions containing anticoagulant proteins such as Protein C and Protein S is in fact highly undesired, as is treatment of thromboembolic disease with compositions containing Factor IX, Factor VII or other procoagulant components as major contaminants. Therefore, the ideal therapeutic composition to correct a deficiency of one specific haemostatic protein should consist of solely that single component in an intact conformation and nothing else except solvent, and sometimes an inert carrier. As a consequence, the purification strategies needed to achieve the desired degree of purity have become increasingly complex.

Along with the introduction of advanced, more complex purification protocols a novel problem of undesired proteolysis of the target species was encountered. Limited proteolysis is a key mechanism in the regulation of a number of biological systems (see H. Neurath and K. A. Walsh, Proc. Natl. Acad. Sci. USA vol 73, 1976, pp 3825–3832). Typical examples of such biological systems include the complement system, the fibrinolytic system, and the blood coagulation system. These biological cascade systems involve the sequential conversion of intact, inactive precursor proteins into active enzymes or cofactors by proteolysis of one or more specific peptide bonds. On the other hand, feedback mechanisms exist to maintain these processes under local control and lead to proteolytic inactivation of the target proteins. Accordingly, the components of the coagulation cascade are present in blood plasma in a precursor form lacking biological activity. With regard to replacement therapy, the presence of coagulation proteins that are no longer intact is troublesome, since after having been subject to limited proteolysis, such cleaved species may bypass the natural, local control of haemostasis in vivo. Although natural mechanisms effectively control proteolysis under physiological conditions, these can no longer be maintained when haemostatic proteins are isolated from their natural source. As such protease-sensitive sequences are exposed within the tertiairy structure of these proteins, they provide easily accessible targets for proteolysis in a non-physiological environment lacking natural control mechanisms. Therefore, it is virtually impossible to completely prevent partial proteolysis during purification. Uncontrolled proteolysis of these vulnerable proteins is not limited to purification from a natural source as human plasma or fractions thereof, but may equally occur when the same proteins are obtained by recombinant DNA technology from transformed cell lines in vitro, or from biological fluids, including milk, of transgenic animals in vivo.

The presence of cleaved species in therapeutic products is clearly not desired, because the presence of activated proteins may trigger thrombogenic responses of the haemostatic system, whereas the presence of inactivated proteins leads to products with suboptimal biological activity that may competitively inhibit the reactions to be corrected. Prothrombin complex concentrates contain activated species of virtually all vitamin K-dependent coagulation factors, and this has been established as a causative agent for the occurrence of thromboembolic complications since the 1970s is (G. C. White et al., Blood vol 49, 1977, pp 159–170; J. M. Lusher, Seminars in Hematology vol 28, suppl 6, 1991, pp 3–5). Theoretically, in particular those species that participate in the initiation phase of the coagulation system, and thereby are the most amplified in the cascade mechanism, are to be considered as the most potent in disturbing the physiological haemostatic balance. Indeed, in vivo studies employing purified activated coagulation factors have identified activated Factor IX (S. Gitel et al., Proc. Natl. Acad. Sci. USA vol 74, 1977, pp 3028–3032) and activated Factor VII (K. Mertens et al., Thromb. Haemostasis vol 64, 1990, pp 138–144) as thrombogenic even in extremely low dosage. This may raise particular concern for activated forms that are relatively resistent to inhibition in vivo. Most activated vitamin K-dependent coagulation factors are subject to almost instantaneous inhibition by the abundance of protease inhibitors in blood plasma. However, Factor IXa is only slowly inhibited, whereas Factor VIIa and activated Protein C have in vivo half-lives up to 2 hours (K. Mertens et al., Thromb. Haemostasis vol 64, 1990, pp 138–144; P. C. Comp, Hematology, McGraw-Hill, New York, N.Y., 1990, pp 1290–1303). Thus, upon infusing vitamin K-dependent haemostatic proteins into patients, it should be noted that even traces of activated forms may remain in the patients circulation sufficiently long to bypass physiological control. Therefore, Protein C and Factors VII and IX are among the proteins that should be prevented from being activated, or should be purified employing a strategy that is selective for their intact zymogens. On the other hand, other cleavages can occur that result in the inactivation of said proteins, thus reducing their therapeutic efficacy. For instance, Factor IX can be inactivated by the enzymes thrombin or elastase, and the cleavage product has no longer the potential of being converted into a form having Factor IXa activity (A. Takaki et al., J. Clin. Invest. vol 72, 1983, pp 1706–1715; W. Kisiel et al., Blood vol 66, 1985, pp 1302–1308). Similarly, the anticoagulant Protein S is readily cleaved by thrombin into a product that no longer has anticoagulant activity (for review see M. Hessing, Biochem. J. vol 277, 1991, pp 581–592). It thus appears highly important to avoid the occurrence of cleaved, non-intact species to reduce side-effects and to improve efficacy of therapeutic concentrates of these factors.

To better appreciate the structural differences between the intact zymogen species and their cleaved derivatives, the molecular events associated with limited proteolysis of these proteins are now described in more detail. Table I presents an overview of target sequences for limited proteolysis as they occur in a number of vitamin K-dependent proteins involved in the haemostatic system. These include:

(a) Human Factor VII: The intact zymogen is a single-chain glycoprotein of 406 amino acids, which is converted to Factor VIIa by the cleavage of a single bond between residues 152 and 153 (see Table I). This target sequence can be cleaved by a number of enzymes, including thrombin and Factors IXa, Xa and XIIa, which results in the activated species which consists of two polypeptide chains that are held together by a disulfide bond. This Factor VIIa provides a powerful thrombogenic trigger by activating a number of target substrates, including Factor X and Factor IX (B. Osterud and S. I. Rapaport, Proc. Natl. Acad. Sci. USA vol 74; 1977, pp 5260–5264).

(b) Human Factor IX: The intact zymogen is a single-chain glycoprotein of 415 amino acids, which is converted into Factor IXa by Factor XIa or Factor VIIa in two steps. The first step involves the cleavage between residues 145 and 146, which results in the formation of a two-chain inactive intermediate (called Factor IXα) containing a light chain of residues 1–145 and a heavy chain of residues 146–415. In the second step, the heavy chain of Factor IXα is further cleaved between residues 180 and 181, resulting in a 35-residue (146–180) activation peptide and an active enzyme (Factor IXaβ) with the remaining heavy chain of residues 181–415. It should be noted that whereas the latter cleavage is required to develop the final Factor IXa activity, the prior cleavage of the 145–146 bond seems to be an obligatory step in Factor IX activation by Factor XIa or Factor VIIa (U. Hedner and E. W. Davie, in: R. W. Colman et al. (Eds), Hemostasis and Thrombosis, J. B. Lippincott, Philadelphia, 1987, pp 29–38; M. J. Griffith et al., J. Clin. Invest. vol 75, 1985, pp 4–10). Therefore, Factor IXα is even more vulnerable than the intact Factor IX zymogen with respect to cleavage at the 180–181 position and the concurrent formation of a thrombogenic Factor IXa species. In addition to this proteolytic activation, also inactivation may occur as the result of cleavage by thrombin or elastase. This proteolytic inactivation involves cleavage between residues 327 and 328, and between residues 338 and 339, resulting in derivatives that can no longer be converted to species with Factor IX procoagulant activity (see Table I).

(c) Human Protein C: The intact zymogen is a two-chain glycoprotein of 419 amino acids, consisting of a light chain of residues 1–155 and a heavy chain of residues 158–419. The zymogen is activated by a single cleavage in the heavy chain, between residues 169 and 170. The activated species is a powerful anticoagulant, which inactivates Factors Va and VIIIa in a manner requiring the presence of a vitamin K-dependent cofactor, called Protein S.

(d) Human Protein S: The intact species is a single-chain glycoprotein of 635 amino acid residues. The N-terminal portion of the protein contains two thrombin-sensitive bonds between residues 49–50 and 70–71. After cleavage of Protein S by thrombin, the N-terminal fragment still is connected to the molecule via a disulfide bond. However, only Protein S that is uncleaved within the thrombin-sensitive region is active as a cofactor for activated Protein C. Therefore, it is preferred to provide intact, uncleaved Protein S in a composition for effective treatment of heriditary or acquired Protein S deficiency.

In conclusion, a special need exists for purification methods that allow the selection of uncleaved, intact species from a source containing the intact proteins as well as proteolytic derivatives generated by cleavage at the target peptide bonds that are summarized in Table I.

TABLE I

Major cleavage sites in vitamin K-dependent proteins and synthetic peptides comprising them[1]

| peptide no.: | | |
|---|---|---|
| | Factor IX activation sites: | |
| 1 | PAVPFPCGRVSVSQTSKLTR$^{145}$↓AETVFPDVDYVNSTEAETIL<br>Q$^{139}$----------D$^{154}$ | SEQ ID NO 9 |
| 2 | AETILDNITQSTQSFNFTR$^{180}$↓VVGGEDAKPGQFPWQVVLNG<br>Q$^{173}$----------K$^{188}$ | SEQ ID NO 10 |
| | Factor IX degradation sites: | |
| 3 | SGWGRVFHKGRSALVLQYLR$^{327}$↓VPLVDRATCLRSTKFTIYNN<br>A$^{320}$----------T$^{335}$ | SEQ ID NO 11 |
| 4 | SALVLQYLRVPLVDRATCLR$^{338}$↓STKFTIYNNMFCAGFHEGGR<br>T$^{335}$-------F$^{342}$ | SEQ ID NO 12 |
| | Factor VII activation site: | |
| 5 | YPCGKIPILEKRNASKPQGR$^{152}$↓IVGGKVCPKGECPWQVLLLV<br>S$^{147}$----------V$^{158}$ | SEQ ID NO 13 |
| | Protein C activation site: | |
| 6 | DTEDQEDQVDPR$^{169}$↓LIDGKMTRRGDSPWQVVLLD<br>E$^{160}$----------G$^{179}$ | SEQ ID NO 14 |
| | Protein S degradation sites: | |
| 7 | VFENDPETDYFYPKYLVCLR$^{49}$↓SFQTGLFTAARQSTNAYPDL<br>F$^{40}$----------A$^{59}$ | SEQ ID NO 15 |
| 8 | FQTGLFTAARQSTNAYPDLR$^{70}$↓SCVNAIPDQCSPLPCNEDGY<br>S$^{62}$----------Q$^{79}$ | SEQ ID NO 16 |

[1](see E.W. Davie et al., in: R.W. Colman et al. (Eds), Hemostasis and Thrombosis, J.B. Lippincott, Philadelphia, 1987, pp 242–267).

DESCRIPTION OF THE PRIOR ART

The development of monoclonal antibody technology has radically changed the potential for purifying trace proteins from plasma to near homogeneity. Monoclonal antibodies can be prepared and selected in such a manner that they show complete specificity towards an individual plasma protein. When a monoclonal antibody specific for a plasma protein is immobilized on an inert matrix, it will absorb that plasma protein specifically from a mixture containing that plasma protein. After washing the matrix, the plasma protein may be eluted under fairly mild conditions in pure or virtually pure form. This approach has allowed the isolation of pure Factor IX from human blood plasma by immuno-affinity chromatography (A. H. Goodall et al., Protides of the Biological Fluids (Peeters, Ed.) vol 30; Pergamon Press, Oxford, 1982, pp 403–407; K. Mertens et al., Thromb. Haemostasis vol 50; 1983, p 249; K. Mertens, Ph.D. dissertation, State University of Leiden, 1985, pp 83–98). Similar methods of immuno-affinity chromatography have subsequently become available for purification of the other vitamin K-dependent haemostatic proteins.

In some cases, a more restricted specificity has been achieved, in that antibodies may specifically bind to their target vitamin K-dependent protein in the presence of $Ca^{2+}$-ions. Under these conditions, the target proteins are in a biologically active conformation by virtue of the interaction of $Ca^{2+}$-ions with the carboxylated glutamic acid residues that are unique to the vitamin K-dependent proteins. When applied in a purification process, such antibodies allow elution of the target protein under mild conditions by the $Ca^{2+}$-binding agent EDTA, as has been described for Factor IX (H. A. Liebman et al., Proc. Natl. Acad. Sci. USA vol 82, 1985, pp 3879–3883; K. J. Smith, Blood vol 72, 1988, pp 1269–1277) as well as for Protein C (D. J. Stearns et al., J. Biol. Chem. vol 263, 1988, pp 826–832).

However, in spite of their high selectivity, those procedures have not been able to distinguish between the intact and activated or degraded coagulation factors, and as a consequence cleaved products are co-purified with the desired intact, non-activated target product. Moreover, antibodies that are $Ca^{2+}$-dependent have the disadvantage that $Ca^{2+}$-ions cannot be added to most source materials, including plasma or fractions thereof, without simultaneously triggering the $Ca^{2+}$-dependent coagulation system that leads to proteolytic cleavage of the vitamin K-dependent target proteins. This represents a major drawback for the applicability of the final therapeutic product as it has been demonstrated that even small amounts of activated coagulation factors have been implicated as causative agents for disseminated intravascular coagulation and thromboembolism.

SUMMARY OF THE INVENTION

The present invention relates to methods for the generation and selection of $Ca^{2+}$-independent, monospecific antibodies (either polyclonal or monoclonal) specific for defined epitopes covering intact (activation or degradation) cleavage sites of haemostatic proteins such as, for example, coagulation Factor IX and Protein S, for the isolation of these proteins as intact, uncleaved polypeptides. The strategy of this method is based on the notion that disruption of the primary sequence of the target protein leads to a number of changes within the protein, one being the exposition of the cleavage site itself. The present invention demonstrates that antibodies against epitopes covering intact cleavage sites may have different affinity for intact and cleaved forms of the epitope, thus allowing separation when applied in a chromatographic process. In order to be applicable in purification processes from a variety of sources, the antibodies described in the present invention are not only specific for a sequence that provides a target for limited proteolysis within the coagulation factor to be isolated, but are also $Ca^{2+}$- independent. The method involves the selection of antibodies with appropriate specificity, immobilization thereof on a solid support, and then contacting a source material with the immobilized antibody to bind said protein. After washing and elution with an appropriate solution, the target protein is recovered in a highly purified form, in a non-activated, intact state that is of particular interest for use in a therapeutic composition for the treatment of haemostatic disorders.

The process of the present invention is a major breakthrough in the field of immuno-affinity chromatography in that it achieves unique selectivity for intact, non-cleaved target proteins. This allows for methods to obtain intact haemostatic proteins, which can thereafter be formulated into improved therapeutic blood products. These products provide safer and more effective agents than are available thus far for the treatment of patients encountering critical bleeding or clotting episodes.

Other objects and advantages of the present invention will become evident from the following detailed description of the invention.

DETAILED DESCRIPTION OF THE PREFERRED EMBODIMENTS

The invention provides a method for isolating a haemostatic protein which is susceptible to proteolytic cleavage, from a mixture containing said protein, comprising subjecting said mixture to immunoaffinity chromatography using a $Ca^{2+}$-independent antibody which substantially distinguishes between intact and cleaved species of said haemostatic protein.

The term "haemostatic protein" is used herein in a broad sense and covers not only blood coagulation factors such as Factors IX and VII, but also vitamin K-dependent proteins such as Proteins C and S which are components of a system acting as an antagonist of the coagulation pathway. Further, although this invention covers the isolation of haemostatic proteins of any origin, which may be any mammal, it is preferably applied to the isolation of haemostatic proteins of human origin.

The antibody used according to this invention may be a polyclonal antibody, but it is preferred to use a monoclonal antibody. The antibody is preferably $Ca^{2+}$-independent and directed against an epitope of said haemostatic protein which covers an intact proteolytic cleavage site in said haemostatic protein. The invention also covers the antibody as such, i.e. a $Ca^{2+}$-independent antibody specific for a haemostatic protein which is susceptible to proteolytic cleavage, wherein said antibody substantially distinguishes between intact and cleaved species of said haemostatic protein.

In a first set of particularly preferred embodiments of the invention, the antibody is specific for Factor IX and reactive with either an oligopeptide having the amino acid sequence QTSKLTRAETVFPDVD (SEQ ID NO:1) corresponding to the amino acid residues 139–154 of Factor IX, or an oligopeptide having the amino acid sequence QSFNDFTRVVGGEDAK (SEQ ID NO:2) corresponding to the amino acid residues 173–188 of Factor IX, or an oligopeptide having the amino acid sequence ALVLQYLRVPLVDRAT (SEQ ID NO:3) corresponding to the amino acid residues 320–335 of Factor IX, or an oligopeptide having the amino acid sequence TCLRSTKF (SEQ ID NO:4) corresponding to the amino acid residues 335–342 of Factor IX.

According to another particularly preferred embodiment of the invention, the antibody is specific for Factor VII and reactive with an oligopeptide having the amino acid sequence SKPQGRIVGGKV (SEQ ID NO:5) corresponding to the amino acid residues 147–158 of Factor VII.

According to yet another particularly preferred embodiment of the invention, the antibody is specific for Protein C and reactive with an oligopeptide having the amino acid sequence EDQEDQVDPRLIDGKMTRRG (SEQ ID NO:6) corresponding to the amino acid residues 160–179 of Protein C.

In a further set of particularly preferred embodiments of the invention, the antibody is specific for Protein S and reactive with either an oligopeptide having the amino acid sequence FYPKYLVCLRSFQTGLFTAA (SEQ ID NO:7) corresponding to the amino acid residues 40–59 of Protein S, or an oligopeptide having the amino acid sequence STNAYPDLRSCVNAIPDQ (SEQ ID NO:8) corresponding to the amino acid residues 62–79 of Protein S.

The invention also provides a method for preparing an antibody which is specific for a haemostatic protein which is susceptible to proteolytic cleavage, wherein said antibody substantially distinguishes between intact and cleaved species of said haemostatic protein, comprising the steps of isolating antibodies which are specific for said haemostatic protein from animals appropriately immunized to induce said haemostatic protein-specific antibodies, or from cell cultures producing said haemostatic protein-specific antibodies, and screening said antibodies to select an antibody which substantially distinguishes between intact and cleaved species of said haemostatic protein.

According to the invention, said screening is preferably carried out with an oligopeptide comprising an amino acid sequence of an epitope of said haemostatic protein which covers an intact proteolytic cleavage site in said haemostatic protein. Said oligopeptide is preferably selected from the group consisting of QTSKLTRAETVFPDVD (SEQ ID NO:1); QSFNDFTRVVGGEDAK (SEQ ID NO:2); ALVLQYLRVPLVDRAT (SEQ ID NO:3); TCLRSTKF (SEQ ID NO:4); SKPQGRIVGGKV (SEQ ID NO:5); EDQEDQVDPRLIDGKMTRRG (SEQ ID NO:6); FYPKYLVCLRSFQTGLFTAA (SEQ ID NO:7); and STNAYPDLRSCVNAIPDQ (SEQ ID NO:8). The invention also covers the oligopeptides as such.

The preparation and characterization of monoclonal antibodies specific for coagulation factors with intact (activation or degradation) cleavage site(s) can be realized by the following screening procedure:

1. Definition of a peptide comprising at least part of the cleavage sequence residues −20 to +20, preferably residues −10 to +10, as counted from the target peptide bond.
2. Screening of culture supernatants of hybridomas for synthesis of antibodies binding to the original antigen (present at least partially as intact protein) in the absence of $Ca^{2+}$-ions, using standard enzyme immuno assay, radioimmunoassay, immunoblotting or suitable technology.
3. Rescreening of positive supernatants with defined peptides comprising relevant activation and/or degradation cleavage sites. The peptides may either be obtained by peptide synthesis, as fragments from the original antigen, or from other sources including those obtained via recombinant DNA technology. In particular cases the peptides may be coupled to suitable carrier molecules.
4. Selection and expansion of the appropriate cell line and application of the selected antibody in an appropriate affinity chromatography process.

The invention also provides a pharmaceutical composition comprising a therapeutically effective amount of a haemostatic protein which is susceptible to proteolytic cleavage and a pharmaceutically acceptable carrier therefor, said haemostatic protein being substantially devoid of proteolytic cleavage products thereof. More particularly, said composition contains haemostatic protein obtained from a mixture containing it by subjecting said mixture to immunoaffinity chromatography using an antibody which substantially distinguishes between intact and cleaved species of said haemostatic protein. Preferably, said haemostatic protein is selected from the class of vitamin K-dependent proteins including Factor IX, Factor VII, Protein C and Protein S.

The invention also covers a haemostatic protein selected from the class of vitamin K-dependent proteins including Factor IX, Factor VII, Protein C and Protein S, said protein being substantially devoid of proteolytic cleavage products thereof.

This invention is illustrated in the Examples for Factor IX and Protein S, but can equally be applied to other haemostatic proteins as will be understood by persons skilled in the art.

The Examples provide details of the manner in which the embodiments of the present invention may be made and used in order to achieve the generation of $Ca^{2+}$-independent monoclonal antibodies substantially specific for intact protein species containing the uncleaved target sequence. The specificity for the intact species implies that the affinity for the intact epitope differs substantially from that for the cleaved epitope. This means that the antibody binds intact species with either higher or lower affinity than the cleaved species, the difference allowing separation of these species in a chromatographic process. These antibodies thus provide novel tools for the isolation of intact haemostatic proteins. For example, the description given in Example I, while exemplary of the present invention as applied to the generation and selection of monoclonal antibodies against the primary activation cleavage site of Factor IX, and their application for the isolation of intact Factor IX, is construed to be applicable to other haemostatic proteins, including Protein S, Factor VII and Protein C. Variations within the purview of one skilled in this art are to be considered to fall within the scope of the present invention. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

EXAMPLE 1

Preparation and selection of $Ca^{2+}$-independent monoclonal antibodies specific for intact human Factor IX For the selection of $Ca^{2+}$-independent monoclonal antibodies with substantial specificity for intact human Factor IX, peptide No. 1 (see Table I) comprising the primary activation site $Q^{139}$-$D^{154}$ of Factor IX was synthesized by standard procedures. Immunization, fusion and subcloning of selected anti-Factor IX positive cultures was performed according to established procedures (G. Köhler and C. Milstein, Nature vol 256; 1975, pp 495–497), employing conventionally purified Factor IX as the antigen. Primary screening of the hybridoma cell supernatants was performed using a solid phase enzyme-linked immunosorbent assay (ELISA). To this end, purified factor IX was coated to the wells of microtiter plates (Dynatech GmbH, Plockingen, Germany) at a concentration of 0.5 $\mu$g/ml in 50 mM $NaHCO_3$ pH 9.5 overnight at 4° C. The plates were washed with 50 mM Tris-HCl, 154 mM NaCl, 10 mM EDTA, 0.05% Tween-20, pH 8.0 and then incubated with culture supernatants in the absence of $Ca^{2+}$-ions. Bound antibodies were detected by peroxidase-conjugated goat anti-mouse antibodies using tetramethylbenzidine as substrate. For the secondary screening, positive supernatants were rescreened using the same ELISA procedure, but with peptide No. 1 conjugated to a bovine albumin carrier (5 $\mu$g/ml) replacing the Factor IX coating. Two positive cell lines (designated CLB-FIX D4 and CLB-FIX 9) were obtained that were reactive with both Factor IX and the synthetic peptide No. 1 covering the primary activation site. The produced immunoglobulins were purified by ion-exchange chromatography and gel filtration using conventional procedures.

The monoclonal antibodies CLB-FIX D4 and CLB-FIX 9 were subtyped and identified as belonging to the IgG1 subclass with a kappa light chain using a mouse MAb isotyping kit (Holland Biotechnology, Leiden, The Netherlands). The two monoclonal antibodies were further characterized with respect to their affinity for intact Factor IX and the cleaved species Factor IX$\alpha$ and Factor IXa$\beta$, employing an ELISA technique as described (Kim et al., J. Immunol. Methods vol 131, 1990, pp 213–222). For both antibodies, the dissociation constant for the complex between antibody and intact Factor IX was found to be 1.2 nM, whereas the affinity for Factor IXa$\beta$ appeared to be negligible (dissociation constant higher than 10 $\mu$M). Both antibody CLB-FIX D4 and CLB-FIX 9 bound to the cleaved species Factor IX$\alpha$ with substantially higher affinity (dissociation constants 0.3 and 0.6 nM, respectively) than to the intact species. These findings demonstrate that cleavage within the epitope of these antibodies results in an alteration of their affinity by at least 2- or 4-fold. The monoclonal antibody CLB-FIX D4 was further examined for its effect on Factor IX clotting activity. A fixed amount of Factor IX (1 $\mu$g) was incubated with varying amounts of antibody CLB-FIX D4 (0–50 $\mu$g) at 37° C. for 30 minutes. Subsequently, residual activity was measured in a one stage coagulation assay (J. J. Veltkamp et al., Thromb. Diath. Haemorrh. vol 19; 1968, pp 279–203). In the presence of a 10-fold molar excess of antibody, Factor IX activity was inhibited by more than 90%, thus confirming that cleavage within the epitope of antibody CLB-FIX D4 is rate-limiting in Factor IX activation. Immunoadsorbents were prepared by coupling the purified CLB-FIX D4 and CLB-FIX 9 IgG's to CNBr-activated Sepharose (5 mg/ml Sepharose; Pharmacia, Uppsala, Sweden) according to standard procedures. The immunosorbents were packed into columns and equilibrated with a buffer consisting of 20 mM trisodiumcitrate, 154 mM NaCl, 10 mM benzamidine-HCl, pH 7.4 for use in affinity chromatography as described below.

EXAMPLE 2

Purification of intact Factor IX from prothrombin complex concentrate

The immobilized CLB-FIX D4 IgG was evaluated for use as an immunosorbent for the isolation of intact factor IX from a prothrombin complex concentrate prepared by conventional techniques (J. Heystek et al., Vox Sang. vol 25; 1973, pp 113–123) as a source material. To 350 ml of prothrombin complex concentrate, 90 ml were added of a buffer containing 0.1 M trisodiumcitrate, 0.77 M NaCl and 0.05 M benzamidine-HCl, pH 7.4. The mixture was applied to a column containing 20 ml of CLB-FIX D4-Sepharose (diameter 2.5 cm, flow rate 25 cm/hr) equilibrated in 20 mM trisodiumcitrate, 154 mM NaCl, 10 mM benzamidine-HCl, pH 7.4. The column was subsequently washed with the same buffer until all unbound protein was removed. At this point the buffer was changed to elution buffer (2 M KSCN in equilibration buffer). Fractions were collected and assayed for protein and Factor IX clotting activity by established procedures (M. M. Bradford, Anal. Biochem. vol 72; 1976, pp 248–254; J. J. Veltkamp et al., Thromb. Diath. Haemorrh. vol 19; 1968, pp 279–203). In the eluate 67% of the Factor IX activity was recovered, with a specific activity of 356 U/mg. The eluate was free of any detectable Factor IXa activity (i.e. <5 pM) as assayed employing a spectrophotometric method (K. Mertens et al., Thromb. Haemostasis vol 54; 1985, pp 654–660). In addition, the non-activated Factor IX product was examined for the presence of Factor II, Factor X and traces of mouse IgG using standard methods. The results demonstrate that the residual amounts of these potential contaminants in the product are extremely low (see Table II).

Similar results were obtained when the same procedure was performed by using the immobilized antibody CLB-FIX 9 under identical conditions as described above for antibody CLB-FIX D4. In addition to KSCN, also other chaotropic salts such as LiCl and $NaNO_3$ could be used in the elution buffer for effectively recovering pure, intact Factor IX.

These results were confirmed by SDS-polyacrylamide gel electrophoresis (K. Weber and M. Osborn, J. Biol. Chem. vol 244; 1969, pp 4406–4412) and Western-blotting analysis (H. Towbin et al., Proc. Natl. Acad. Sci. USA vol 76; 1979, pp 4350–4355) employing appropriate antibodies against Factors II, IX, X, Protein C and Protein S. The analysis of flowthrough fractions demonstrated the presence of large amounts of the vitamin K-dependent proteins Factors II, X, Protein C and S. Using polyclonal antibodies against Factor IX, a number of two-chain species representing Factor IX activation products could be visualized as well as some apparently non-bound single-chain species. In contrast, the eluted fractions contained exclusively the non-activated, intact Factor IX species. No contaminants could be detected, thereby confirming the quantitative analysis shown in Table II. Affinity chromatography employing antibodies CLB-FIX D4 or CLB-FIX 9 thus provides an effective method for the specific isolation of non-activated Factor IX from prothrombin complex concentrate.

TABLE II

Purification of intact Factor IX from prothrombin complex concentrate (PCC)

| Source | Volume (ml) | Protein (mg/ml) | FIX (U/ml) | FII (U/ml) | FX (U/ml) | mouse IgG (μg/ml) |
|---|---|---|---|---|---|---|
| PCC | 350 | 20.2 | 39.1 | 62.5 | 64.1 | n.d. |
| Flow through | 440 | 14.7 | 10.4 | 49.7 | 51.0 | n.d. |
| Eluate | 73 | 0.28 | 98.7 | <0.008 | <0.003 | <0.1 |

n.d.: not determined.

EXAMPLE 3

Selective purification of intact Factor IX from a mixture of partially cleaved Factor IX species As affinity chromatography employing antibody CLB-FIX D4 permits the specific separation of apparently non-activated Factor IX from other haemostatic proteins (see Example I), its selectivity for the various Factor IX cleavage products was evaluated in more detail, with special reference to Factor IXaβ and its proteolysis-sensitive precursor Factor IXα.

Three mixtures were prepared for subjection to CLB-FIX D4-affinity chromatography, each consisting to a major extent of one specific Factor IX activation product:

(1) Factor IXaβ: Purified Factor IX, as obtained by the method of Example I, was activated by incubation with purified human Factor XIa. The latter was prepared from Celite-activated human plasma (D. L. Tankersley et al., Thromb. Res. vol 25; 1982, pp 307–317) by immuno-affinity chromatography using a monoclonal antibody against human Factor XI (J. C. M. Meijers, Ph.D. dissertation, State University of Utrecht, 1988, pp 93–108). Factor IX (245 μg/ml) was incubated with Factor XIa (16 μg/ml) in 50 mM Tris, 100 mM NaCl, pH 7.4 containing $CaCl_2$ (2 mM). After incubation for 2 hours at 37° C., the reaction was terminated by the addition of EDTA (10 mM final concentration), and the mixture was subjected to CLB-FIX D4-chromatography as described below. At this stage, about 90% of the Factor IX had been converted into Factor IXaβ as judged by SDS-polyacrylamide gel electrophoresis and Western-blotting analysis.

(2) Factor IXα: For the preparation of Factor IXα, Factor IX was incubated with Factor XIa under the same conditions as described above for Factor IXaβ, except that $CaCl_2$ was replaced by $MnCl_2$ (6.8 mM) during incubation. Under these conditions, Factor IXα was found to accumulate as the major cleavage product, while no substantial Factor IXa formation could be detected. After incubation for 2 hours at 37° C., EDTA was added to 10 mM final concentration, and the mixture was subjected to CLB-FIX D4-chromatography. SDS-polyacrylamide gel electrophoresis and Western-blotting analysis revealed that about 70% of the protein had been converted to the two-chain Factor IXα by a single cleavage at the 145–146 position (see Table I).

(3) Factor IX: As a control, the same amount of purified Factor IX was incubated in the absence of Factor XIa prior to subjection to CLB-FIX D4-chromatography.

These mixtures (2.4 ml) were subsequently applied to an anti-Factor IX CLB-FIX D4 IgG column (volume 3 ml; diameter 1 cm, flow rate 10 ml/hour). The column was washed and eluted as described in Example I. The protein content and activity of Factor IX and Factor IXa in flowthrough and eluate were determined using the same methods as in Example I. Table III summarizes these experiments and demonstrates that Factor IXaβ did not bind to the anti-Factor IX monoclonal antibody column, whereas residual non-activated, intact Factor IX was recovered in the eluate. The observation that the intermediate cleavage product Factor IXα was not eluted from the affinity column, supports the concept that monoclonal antibodies which substantially distinguish between intact Factor IX and species that are cleaved at the primary activation site between residues 145–146, may be employed in a chromatographic process for specifically isolating intact Factor IX.

The evidence presented here demonstrates for the first time the utilization of a $Ca^{2+}$-independent monoclonal antibody specific for an epitope comprising an intact cleavage site for the isolation of Factor IX that is, by all the criteria employed herein, essentially free of other plasma proteins, and at the same time also entirely intact and free from activated species or activation intermediates. The Factor IX product being devoid of any thrombogenic contaminants, it provides a major improvement over Factor IX preparations heretofore known in the art for use in replacement therapy in patients afflicted with haemophilia B.

TABLE III

Selective purification of intact Factor IX from mixtures containing cleaved Factor IX species

| Applied Factor IX species | Recovered Factor IX species | | | | | |
|---|---|---|---|---|---|---|
| | Protein (μg) | | Intact FIX (μg) | | FIXaβ (μg) | |
| | Unbound | Eluted | Unbound | Eluted | Unbound | Eluted |
| Factor IXaβ | 566 | 62 | —(1) | 50 | 550 | <0.001 |
| Factor IXα | <10 | 92(3) | —(2) | 85 | 7 | <0.001 |
| Factor IX | 20 | 580 | 23 | 588 | <0.001 | <0.001 |

— intact Factor IX not measurable due to the presence of Factor IXaβ(1) and Factor IXα(2).
(3)Number refers to protein eluted in 2M KSCN containing buffer; non-eluted protein representing Factor IXα could subsequently be eluted in the same buffer containing 3M KSCN.

EXAMPLE 4

Preparation and selection of monoclonal antibodies specific for intact human Protein S For the selection of $Ca^{2+}$-independent monoclonal antibodies specifically recognizing intact human Protein S, peptide No. 7 (see Table I) comprising the primary cleavage site $F^{40}$-$A^{59}$ of Protein S was synthesized by standard procedures. Immunization, fusion and subcloning of selected anti-Protein S positive cultures were performed employing conventionally purified Protein S (Dahlbäck, Biochem. J. vol 209; 1983, pp 837–846) as the antigen. Primary screening of anti-Protein S monoclonal antibody secreting cell lines was performed using an anti-Protein S specific ELISA system in the absence of $Ca^{2+}$-ions, essentially as described in Example 1. For the secondary screening, positive supernatants were rescreened using the same ELISA procedure, but with peptide No. 7 replacing the Protein S coating. Two positive cell lines (designated CLB-PS 41 and CLB-PS 52) were obtained that were reactive with both Protein S and the synthetic peptide No. 7 covering the cleavage site $F^{40}$-$A^{59}$.

The monoclonal antibodies were further characterized with respect to their selectivity for intact Protein S within a mixture of cleaved Protein S species. For this purpose, purified Protein S was converted into its cleaved form by incubating Protein S (140 μg/ml) with thrombin (0.75 μg/ml) in 50 mM Tris, 150 mM NaCl, pH 7.4. During incubation for 1 hour at 37° C., Protein S was cleaved into its two-chain derivative as judged by SDS-polyacrylamide gel electrophoresis. However, ELISA analysis (see Example 1) employing the antibodies CLB-PS 41 or CLB-PS 52 as the first, immobilized antibody revealed that, in parallel with the extent of proteolysis observed, the recognition of Protein S was abolished. These findings demonstrate that cleavage within the epitope of these antibodies results in a substantial alteration of their affinity for Protein S. The lack of binding of antibodies CLB-PS 41 and CLB-PS 52 to cleaved Protein S species is in agreement with their epitope being located at the primary cleavage site $F^{40}$-$A^{59}$ as represented by peptide No. 7. The produced immunoglobulins were purified and immunoadsorbents were prepared by coupling 5 mg of the purified CLB-PS 41 and CLB-PS 52 IgG's to 0.3 g of CNBr-activated Sepharose as described in Example 1. The immunosorbents were packed into columns and equilibrated with a buffer consisting of 20 mM trisodiumcitrate, 154 mM NaCl, 10 mM benzamidine-HCl, pH 7.4 for use in affinity chromatography as described below.

EXAMPLE 5

Purification of intact Protein S from human plasma

Citrated human plasma (100 ml) was applied to the anti-Protein S CLB-PS 52 IgG column (column volume 3 ml; diameter 1 cm; flow rate 10 ml/h). The column was washed with equilibration buffer until all unbound protein was removed. At this point the buffer was changed to dissociation buffer (3 M KSCN in equilibration buffer). Fractions were collected for analysis of protein content, composition by SDS-polyacrylamide gel electrophoresis and Western-blotting analysis, and of Protein S cofactor activity for activated Protein C (P. C. Comp and C. T. Esmon, New Engl. J. Med. vol 311, 1984, pp 1525–1528). Elution yielded a high-molecular weight species that could be identified as a component called C4b-binding protein, which is known to occur in complex with Protein S in plasma (B. Dahlback and J. Stenflo, Proc. Natl. Acad. Sci. USA vol 78, 1981, pp. 2512–2516). However, no intact Protein S could be detected in these fractions, indicating that this had remained bound to the CLB-PS 52 monoclonal antibody column. The buffer was changed back to the equilibration buffer, and subsequently Protein S was eluted using 6 M Guanidine-HCl in the same buffer. Assays for Protein S activity demonstrated that the eluted Protein S product displayed full biological activity. Electrophoretic and Western-blotting analysis under reducing and nonreducing conditions revealed that the final product did not contain any detectable C4b-binding protein or other contaminant, and consisted entirely of single-chain, intact Protein S.

The evidence provided here demonstrates for the first time that it is feasible to isolate Protein S in a completely uncleaved, intact state by virtue of monoclonal antibodies which substantially distinguish between intact Protein S and species that are cleaved at the primary thrombin cleavage activation site between residues 49–50. When applied in an immunoaffinity chromatography process, a Protein S product is obtained that is devoid of any cleaved, inactivated species, and as such provides a major improvement over Protein S preparations heretofore known in the art. This should allow efficient treatment of patients afflicted with thrombosis due to inherited or acquired Protein S deficiency.

It is understood that the examples and embodiments described herein are for illustrative purposes only and that various modifications or changes in light thereof will be suggested to persons skilled in the art and are to be included within the spirit and purview of this application and the scope of the appended claims.

SEQUENCE LISTING (1) GENERAL INFORMATION:

(iii) NUMBER OF SEQUENCES: 16

-continued (2) INFORMATION FOR SEQ ID NO: 1:

(i) SEQUENCE CHARACTERISTICS:
(A) LENGTH: 16 amino acids
(B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 1:

```
Gln Thr Ser Lys Leu Thr Arg Ala Glu Thr Val Phe Pro Asp Val Asp
1               5                   10                  15
```

(2) INFORMATION FOR SEQ ID NO: 2:

(i) SEQUENCE CHARACTERISTICS:
(A) LENGTH: 16 amino acids
(B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 2:

```
Gln Ser Phe Asn Asp Phe Thr Arg Val Val Gly Gly Glu Asp Ala Lys
1               5                   10                  15
```

(2) INFORMATION FOR SEQ ID NO: 3:

(i) SEQUENCE CHARACTERISTICS:
(A) LENGTH: 16 amino acids
(B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 3:

```
Ala Leu Val Leu Gln Tyr Leu Arg Val Pro Leu Val Asp Arg Ala Thr
1               5                   10                  15
```

(2) INFORMATION FOR SEQ ID NO: 4:

(i) SEQUENCE CHARACTERISTICS:
(A) LENGTH: 8 amino acids
(B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 4:

```
Thr Cys Leu Arg Ser Thr Lys Phe
1               5
```

(2) INFORMATION FOR SEQ ID NO: 5:

(i) SEQUENCE CHARACTERISTICS:
(A) LENGTH: 12 amino acids
(B) TYPE: amino acid

-continued (C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 5:

```
Ser Lys Pro Gln Gly Arg Ile Val Gly Gly Lys Val
1               5                   10
```

(2) INFORMATION FOR SEQ ID NO: 6:

(i) SEQUENCE CHARACTERISTICS:
(A) LENGTH: 20 amino acids
(B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 6:

```
Glu Asp Gln Glu Asp Gln Val Asp Pro Arg Leu Ile Asp Gly Lys Met
1               5                   10                  15

Thr Arg Arg Gly
            20
```

(2) INFORMATION FOR SEQ ID NO: 7:

(i) SEQUENCE CHARACTERISTICS:
(A) LENGTH: 20 amino acids
(B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 7:

```
Phe Tyr Pro Lys Tyr Leu Val Cys Leu Arg Ser Phe Gln Thr Gly Leu
1               5                   10                  15

Phe Thr Ala Ala
            20
```

(2) INFORMATION FOR SEQ ID NO: 8:

(i) SEQUENCE CHARACTERISTICS:
(A) LENGTH: 18 amino acids
(B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 8:

```
Ser Thr Asn Ala Tyr Pro Asp Leu Arg Ser Cys Val Asn Ala Ile Pro
1               5                   10                  15

Asp Gln
```

(2) INFORMATION FOR SEQ ID NO: 9:

(i) SEQUENCE CHARACTERISTICS:
(A) LENGTH: 40 amino acids

-continued (B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 9:

```
Pro Ala Val Pro Phe Pro Cys Gly Arg Val Ser Val Ser Gln Thr Ser
1               5                   10                  15

Lys Leu Thr Arg Ala Glu Thr Val Phe Pro Asp Val Asp Tyr Val Asn
            20                  25                  30

Ser Thr Glu Ala Glu Thr Ile Leu
        35                  40
```

(2) INFORMATION FOR SEQ ID NO: 10:

(i) SEQUENCE CHARACTERISTICS:
(A) LENGTH: 40 amino acids
(B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 10:

```
Ala Glu Thr Ile Leu Asp Asn Ile Thr Gln Ser Thr Gln Ser Phe Asn
1               5                   10                  15

Asp Phe Thr Arg Val Val Gly Gly Glu Asp Ala Lys Pro Gly Gln Phe
            20                  25                  30

Pro Trp Gln Val Val Leu Asn Gly
        35                  40
```

(2) INFORMATION FOR SEQ ID NO: 11:

(i) SEQUENCE CHARACTERISTICS:
(A) LENGTH: 40 amino acids
(B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 11:

```
Ser Gly Trp Gly Arg Val Phe His Lys Gly Arg Ser Ala Leu Val Leu
1               5                   10                  15

Gln Tyr Leu Arg Val Pro Leu Val Asp Arg Ala Thr Cys Leu Arg Ser
            20                  25                  30

Thr Lys Phe Thr Ile Tyr Asn Asn
        35                  40
```

(2) INFORMATION FOR SEQ ID NO: 12:

(i) SEQUENCE CHARACTERISTICS:
(A) LENGTH: 40 amino acids
(B) TYPE: amino acid
(C) STRANDEDNESS: unknown
(D) TOPOLOGY: unknown (ii) MOLECULE TYPE: peptide (iii) HYPOTHETICAL: NO -continued (xi) SEQUENCE DESCRIPTION: SEQ ID NO: 12:

```
Ser Ala Leu Val Leu Gln Tyr Leu Arg Val Pro Leu Val Asp Arg Ala
1               5                   10                  15

Thr Cys Leu Arg Ser Thr Lys Phe Thr Ile Tyr Asn Asn Met Phe Cys
            20                  25                  30

Ala Gly Phe His Glu Gly Gly Arg
        35                  40
```

(2) INFORMATION FOR SEQ ID NO: 13:

(i) SEQUENCE CHARACTERISTICS:
(A) LENGTH: 40 amino acids
(B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 13:

```
Tyr Pro Cys Gly Lys Ile Pro Ile Leu Glu Lys Arg Asn Ala Ser Lys
1               5                   10                  15

Pro Gln Gly Arg Ile Val Gly Gly Lys Val Cys Pro Lys Gly Glu Cys
            20                  25                  30

Pro Trp Gln Val Leu Leu Leu Val
        35                  40
```

(2) INFORMATION FOR SEQ ID NO: 14:

(i) SEQUENCE CHARACTERISTICS:
(A) LENGTH: 32 amino acids
(B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 14:

```
Asp Thr Glu Asp Gln Glu Asp Gln Val Asp Pro Arg Leu Ile Asp Gly
1               5                   10                  15

Lys Met Thr Arg Arg Gly Asp Ser Pro Trp Gln Val Val Leu Leu Asp
            20                  25                  30
```

(2) INFORMATION FOR SEQ ID NO: 15:

(i) SEQUENCE CHARACTERISTICS:
(A) LENGTH: 40 amino acids
(B) TYPE: amino acid
(C) STRANDEDNESS: unknown
(D) TOPOLOGY: unknown (ii) MOLECULE TYPE: peptide (iii) HYPOTHETICAL: NO (xi) SEQUENCE DESCRIPTION: SEQ ID NO: 15:

```
Val Phe Glu Asn Asp Pro Glu Thr Asp Tyr Phe Tyr Pro Lys Tyr Leu
1               5                   10                  15

Val Cys Leu Arg Ser Phe Gln Thr Gly Leu Phe Thr Ala Ala Arg Gln
            20                  25                  30

Ser Thr Asn Ala Tyr Pro Asp Leu
```

-continued

```
        35                  40


(2) INFORMATION FOR SEQ ID NO: 16:

     (i) SEQUENCE CHARACTERISTICS:
          (A) LENGTH: 40 amino acids
          (B) TYPE: amino acid
          (C) STRANDEDNESS: unknown
          (D) TOPOLOGY: unknown

    (ii) MOLECULE TYPE: peptide

   (iii) HYPOTHETICAL: NO

    (xi) SEQUENCE DESCRIPTION: SEQ ID NO: 16:

Phe Gln Thr Gly Leu Phe Thr Ala Ala Arg Gln Ser Thr Asn Ala Tyr
1               5                   10                  15

Pro Asp Leu Arg Ser Cys Val Asn Ala Ile Pro Asp Gln Cys Ser Pro
            20                  25                  30

Leu Pro Cys Asn Glu Asp Gly Tyr
        35                  40
```

We claim:

1. A method for isolating haemostatic proteins susceptible to specific proteolytic cleavage, from a mixture containing said proteins comprising subjecting said mixture to immunoaffinity chromatography using a $Ca^{2+}$-independent antibody which binds intact but does not bind cleaved species of said haemostatic proteins, and isolating the haemostatic proteins.

2. A method as claimed in claim 1, wherein said antibody specifically binds epitopes of said haemostatic proteins which covers an intact proteolytic [cleavage sites] *site* in said haemostatic proteins.

3. A method for isolating a haemostatic protein which is susceptible to specific proteolytic cleavage from a mixture containing said protein, wherein the method comprises (a) subjecting said mixture to affinity chromatography using antibodies capable of binding haemostatic protein wherein the antibodies are not Ca++-dependent and wherein the antibodies are capable of specifically binding activated and are not capable of specifically binding non-activated species of said haemostatic protein, and (b) isolating said haemostatic protein.

4. A method in accordance with claim 3 wherein said haemostatic protein is a Vitamin K-dependent protein selected from the group consisting of Factor IX, Factor VII, Protein C and Protein S.

5. A method for isolating a protein selected from the group consisting of Factor IX, Factor VII, Protein C and Protein S from a mixture containing said protein which comprises subjecting said mixture to immunoaffinity chromatography using an antibody capable of binding said protein, said antibody being non $Ca^{2+}$-dependent and capable of binding intact but not cleaved species of said protein resulting from specific proteolytic cleavage of the intact form, and isolating the protein.

6. A method as claimed in claim 3, wherein said antibody is specific for Factor IX and specifically binds an oligopeptide consisting of the amino acid sequence QTSKLTRAETVFPDVD (SEQ ID NO:1) corresponding to the amino acid residues 139–154 of Factor IX.

*7. A method for isolating an uncleaved haemostatic protein susceptible to specific proteolytic cleavage from a mixture containing the uncleaved haemostatic protein and proteolytic cleavage products thereof, the method comprising:*

*immobilizing on a solid support a $Ca^{2+}$-independent antibody having substantially higher affinity for the uncleaved haemostatic protein than for the proteolytic cleavage products;*

*contacting the mixture containing the uncleaved haemostatic protein and proteolytic cleavage products with the immobilized antibody to bind the uncleaved haemostatic protein to the antibody;*

*separating the bound uncleaved haemostatic protein from the proteolytic cleavage products by affinity chromatography; and*

*isolating the uncleaved haemostatic protein.*

*8. A method according to claim 7 wherein the antibody is specific for an epitope that covers an intact proteolytic cleavage site in the uncleaved haemostatic protein.*

*9. A method according to claim 7 wherein the uncleaved haemostatic protein is a blood coagulation factor.*

*10. A method according to claim 9 wherein the blood coagulation factor is Factor IX or Factor VII.*

*11. A method according to claim 7 wherein the uncleaved haemostatic protein is an antagonist of a blood coagulation factor.*

*12. A method according to claim 11 wherein the antagonist of a blood coagulation factor is Protein C or Protein S.*

*13. A method for isolating an uncleaved haemostatic protein susceptible to specific proteolytic cleavage from a mixture containing the uncleaved haemostatic protein and proteolytic cleavage products thereof, the method comprising the steps of:*

*immobilizing on a solid support a $Ca^{2+}$-independent antibody having substantially lower affinity for the uncleaved haemostatic protein than for the proteolytic cleavage products;*

*contacting the mixture containing the uncleaved haemostatic protein and proteolytic cleavage products with the immobilized antibody to bind the proteolytic cleavage products to the antibody;*

*separating the bound proteolytic cleavage products from the uncleaved haemostatic protein by affinity chromatography; and*

*isolating the uncleaved haemostatic protein.*

*14. A method according to claim 13 wherein the antibody is specific for an epitope that covers an intact proteolytic cleavage site in the uncleaved haemostatic protein.*

*15. A method according to claim 13 wherein the uncleaved haemostatic protein is a blood coagulation factor.*

*16. A method according to claim 15 wherein the blood coagulation factor is Factor IX or Factor VII.*

*17. A method according to claim 13 wherein the uncleaved haemostatic protein is an antagonist of a blood coagulation factor.*

*18. A method according to claim 17 wherein the antagonist of a blood coagulation factor is Protein C or Protein S.*

* * * * *

UNITED STATES PATENT AND TRADEMARK OFFICE

CERTIFICATE OF CORRECTION

PATENT NO. : RE 38,202 E
DATED : July 22, 2003
INVENTOR(S) : Mertens et al.

It is certified that error appears in the above-identified patent and that said Letters Patent is hereby corrected as shown below:

Column 1,
Lines 12-13, now reads "application No. 10/228,882" should read -- application No. 10/228,832 --

Column 23,
Line 35, now reads "[cleavage sites] site" should read -- cleavage [sites] site --

Signed and Sealed this

Twenty-first Day of October, 2003

JAMES E. ROGAN
*Director of the United States Patent and Trademark Office*